(12) United States Patent
Yamauchi et al.

(10) Patent No.: US 6,495,712 B2
(45) Date of Patent: Dec. 17, 2002

(54) PROCESS FOR PRODUCTION OF CARBOXYLIC ACID ARYL ESTERS

(75) Inventors: Toshiyuki Yamauchi, Tokyo; Masuo Omichi, Okegawa; Eisuke Kanagawa, Kitamoto; Tomohiro Tanino, Toda; Yoshikatsu Osamura, Kasukabe, all of (JP)

(73) Assignee: Johoku Chemical Co., Ltd., Tokyo (JP)

( * ) Notice: Subject to any disclaimer, the term of this patent is extended or adjusted under 35 U.S.C. 154(b) by 30 days.

(21) Appl. No.: 09/906,748

(22) Filed: Jul. 18, 2001

(65) Prior Publication Data

US 2002/0013491 A1 Jan. 31, 2002

(30) Foreign Application Priority Data

Jul. 19, 2000 (JP) .................................. 2000-219514

(51) Int. Cl.$^7$ ............................................. C07C 69/00
(52) U.S. Cl. ...................................... 560/130; 560/105
(58) Field of Search ................................ 560/105, 130

(56) References Cited

U.S. PATENT DOCUMENTS 5,808,130 A * 9/1998 Krbechek .................... 560/130

* cited by examiner

Primary Examiner—Paul J. Killos
Assistant Examiner—Taylor V Oh
(74) Attorney, Agent, or Firm—Morrison & Foerster LLP

(57) ABSTRACT

A process for production of carboxylic acid aryl esters which comprises reacting a carboxylic acid having at least one carboxyl group with a di- or tri-aryl phosphite compound, in the presence of a basic compound and/or water. The carboxylic acid aryl esters can also be produced by reacting a carboxylic acid or a basic salt thereof with a diaryl phosphite compound.

3 Claims, No Drawings

PROCESS FOR PRODUCTION OF CARBOXYLIC ACID ARYL ESTERS

BACKGROUND OF THE INVENTION

1. Field of the Invention

The present invention relates to a process for production of carboxylic acid aryl esters. More specifically, the invention relates to a process for production of carboxylic acid aryl esters by a novel reaction not known in the prior art.

2. Description of the Related Art

Aryl esterification of carboxylic acids has conventionally been accomplished by a dehydration reaction between carboxylic acids and phenols, by a method such as (1) using a mineral acid as the catalyst or (2) using a dehydrating agent at an equivalent amount or greater. There is also known a method whereby (3) a carboxylic acid halide and a phenol are reacted to obtain a carboxylic acid aryl ester.

The method of (1) can be applied for production of alkyl esters from alkyl alcohols, but has a drawback in that, with phenols, either no reaction occurs or the reaction yield is very poor.

An example of the method of (2) is described in "Organic Compound Syntheses" (Yuki Kagobutsu Goseiho, by the Society of Synthetic Organic Chemistry, Japan) whereby polyphosphoric acid is used as the dehydrating agent, but since this requires use of the polyphosphoric acid in a large amount, the cost is high and waste water treatment also poses a problem. Japanese Unexamined Patent Publication No. 5-84507 discloses the use of dicyclohexylcarbodiimide as a dehydrating agent, but in this case the dehydrating agent is expensive and a problem is posed in economical terms.

For method (3), a number of documents describe halogenation of a carboxylic acid using a halogen compound such as $PCl_3$, $POCl_3$, $PCl_5$ or $SOCl_2$ followed by reaction with a phenol, but the method involves a complex production process, as a two-stage reaction, and is therefore not a preferred choice.

BRIEF SUMMARY OF THE INVENTION

It is an object of the present invention to overcome the problems associated with the prior art by providing a process for production of carboxylic acid aryl esters which is very simple, easy and inexpensive.

In order to achieve this object, the present invention provides a process for production of carboxylic acid aryl esters which comprises reacting a carboxylic acid having at least one carboxyl group with a di- or tri-aryl phosphite compound represented by the following general formula (1):

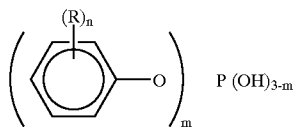

(1)

where each R independently represents a hydrogen atom, halogen or alkyl group, m is 2 or 3 and n is 1, 2, or 3, and when there exist a plurality of halogen and/or an alkyl groups as R, they may be the same or different, in the presence of a basic compound and/or water.

The invention further provides a process for production of carboxylic acid aryl esters which comprises reacting a basic salt of a carboxylic acid having at least one carboxyl group with a diaryl phosphite compound represented by the following general formula (2):

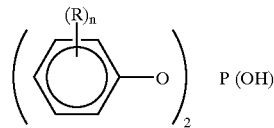

(2)

where each R independently represents a hydrogen atom, halogen or alkyl group, n is 1, 2, or 3, and when there exist a plurality of halogen and/or alkyl groups as R, they may be the same or different.

The invention still further provides a process for production of carboxylic acid aryl esters which comprises reacting a carboxylic acid having at least one carboxyl group with a diaryl phosphite compound represented by general formula (2) above.

DETAILED DESCRIPTION OF THE INVENTION

According to the process of the invention, the reaction may be carried out with the di- or tri-aryl phosphite compound of general formula (1) used in an amount at least equivalent with respect to the carboxyl groups of the carboxylic acid. The reaction is commonly carried out with heating or stirring, and if necessary using a solvent, but the process of the invention is in no way limited to these reaction conditions. The esterification rate will differ slightly depending on the type of carboxylic acid compound used as the starting material, but an esterification rate of 80% or greater, and in most cases 90% or greater, can be easily achieved for a variety of compounds.

Any of various ordinary methods may be employed to recover the desired aryl ester from the reaction system after completion of the reaction. For example, if the reaction product is distillable, it may be distilled off and the product recovered. Alternatively, if the reaction product crystallizes, it may be crystallized out or else dissolved in an appropriate solvent and then cooled to crystallization, and the product recovered.

It has been found that addition of basic compounds or a small amount of water during the process of the invention will promote the reaction. Examples of such basic compounds include alkali metal or alkali earth metal hydroxides, oxides, carbonates and the like.

In the process of the invention, it is believed that when a reaction between the carboxylic acid and a triaryl phosphite compound of general formula (1), where m is 3, is carried out in the presence of a basic compound, a basic salt of the carboxylic acid is produced first while a phenol compound corresponding to a diaryl phosphite compound of general formula (1) where m is 2 is also produced, and then the carboxylic acid basic salt and diaryl phosphite compound in turn react to produce the corresponding carboxylic acid aryl ester and corresponding arylphosphonic acid basic salt. According to the invention, therefore, the target carboxylic acid aryl ester can also be produced by reaction of the carboxylic acid basic salt and diaryl phosphite compound of general formula (1) where m is 2, instead of reaction of the carboxylic acid and triaryl phosphite compound of general formula (1) where m is 3 in the presence of a basic compound. Consequently, the present invention also encompasses a process for production of carboxylic acid aryl esters which comprises reacting the aforementioned carboxylic acid basic salts with diaryl phosphite compounds represented by general formula (2).

On the other hand, it is believed that when the aforementioned carboxylic acid and triaryl phosphite compound of general formula (1), where m is 3, are reacted in the presence of water in the process of the invention, the triaryl phosphite compound first hydrolyzes to produce a diaryl phosphite compound of general formula (1) where m is 2 and the corresponding phenol compound, and then the resulting diaryl phosphite compound and the carboxylic acid react to produce the corresponding carboxylic acid aryl ester and the corresponding arylphosphonic acid. According to the invention, therefore, the target carboxylic acid aryl ester can also be produced by reaction of the carboxylic acid and diaryl phosphite compound of general formula (1) where m is 2, instead of reaction of the carboxylic acid and triaryl phosphite compound of general formula (1) where m is 3 in the presence of water. Consequently, the present invention also encompasses a process for the production of carboxylic acid aryl esters which comprises reacting the aforementioned carboxylic acid with diaryl phosphite compounds represented by general formula (2).

The present invention will now be explained further by way of examples, with the understanding that the invention is in no way limited by these examples.

EXAMPLE 1

Production of phenyl acetate

In a 500 mL four-necked flask equipped with a thermometer, stirrer and reflux condenser there were charged 310 g (1.0 mole) of triphenyl phosphite, 60 g (1.0 mole) of acetic acid and 18 g (1.0 mole) of water, and the mixture was heated while stirring for one hour of reaction at 140–150° C. The reaction solution was analyzed by liquid chromatography and found to have an esterification rate of 97%.

Next, a distillation condenser was mounted in place of the reflux condenser for distillation under reduced pressure at 20 mmHg, and the fraction with a boiling point of 90–93° C. was obtained. The product weight was 120 g, which was a yield of 88%. The purity of the product was 96% according to gas chromatography.

EXAMPLE 2

Production of diphenyl sebacate

In a four-necked flask having the same construction as that used in Example 1 there were charged 310 g (1.0 mole) of triphenyl phosphite, 101 g (0.5 mole) of sebacic acid and 18 g (1.0 mole) of water, and the mixture was heated while stirring for 2 hours of reaction at 120–130° C. The reaction solution was analyzed by liquid chromatography to have an esterification rate of 97%.

Next, 51 g of phenol was recovered from the reaction solution under reduced pressure at 100–110° C.

After then placing 500 mL of isopropyl alcohol (IPA) in a 1L beaker and pouring in the above-mentioned reaction solution while stirring, crystals were precipitated. The crystals were filtered, washed with IPA and dried. The product weight was 134 g which was a yield of 76%, and the melting point was 62–64° C. The purity of the product was 97% according to liquid chromatography.

EXAMPLE 3

Production of carboxybenzotriazole phenyl ester

In a four-necked flask having the same construction as that used in Example 1 there were charged 148.8 g (0.48 mole) of triphenyl phosphite, 65.2 g (0.4 mole) of carboxybenzotriazole and 163 g of phenol as a solvent, and after adding 16.8 g (0.42 mole) of NaOH and 1.5 g (0.08 mole) of water while stirring, the mixture was heated. Upon reaction for 4 hours at 160–165° C. the presence of unreacted carboxybenzotriazole crystals was no longer apparent, and continued reaction for one hour at the same temperature gave an esterification rate of 96%.

After completion of the reaction, the internal temperature was lowered to 120° C., and a distillation condenser was mounted in place of the reflux condenser for distillation removal of the phenol under reduced pressure. The internal temperature was then lowered to 80° C., the reflux condenser was remounted, 200 g of a 50% IPA aqueous solution was added dropwise, and the mixture was allowed to cool. The precipitated crude crystals were filtered off and recovered, and then recrystallized from a 50% IPA aqueous solution. The product weight was 76.5 g, which was a yield of 80%, and the melting point was 172–175° C. The purity of the product was 99% according to liquid chromatography.

EXAMPLE 4

Production of carboxybenzotriazole phenyl ester

The procedure of Example 3 was repeated, except that 26.5 g (0.25 mole) of $Na_2CO_3$ was used instead of NaOH.

The esterification rate was 90%, the product weight was 71.7 g, the yield was 75% and the purity was 99%.

EXAMPLE 5

Production of benzoic acid phenyl ester

In a 300 mL four-necked flask equipped with a thermometer, stirrer and reflux condenser there were charged 46.5 g (0.15 mole) of triphenyl phosphite, 12.2 g (0.1 mole) of benzoic acid and 70 g of cumene as a solvent, and then 4.2 g (0.105 mole) of NaOH and 0.9 g (0.05 mole) of water were added and heating was initiated while stirring. The heating was slowly continued from a temperature of 20° C. to 150° C. over a period of an hour, and then from a temperature of 160–165° C.; upon reaction for 20 hours at that temperature the presence of unreacted benzoic acid crystals was no longer apparent, and the reaction was continued for one hour at the same temperature. Analysis of the reaction solution by liquid chromatography showed disappearance of the benzoic acid starting material and an esterification rate of 80%.

After completion of the reaction, the internal temperature was lowered to 120° C., and a distillation condenser was mounted in place of the reflux condenser for distillation removal of the cumene and phenol under reduced pressure. The internal temperature was then lowered to 80° C., the reflux condenser was remounted, 100 g of hot water was added dropwise to disperse the vessel contents, the mixture was allowed to cool to 10° C., and the crude crystals were filtered off and recovered to obtain 35 g of crude product. After adding 15 g of ethyl alcohol and heating to reflux for 30 minutes, it was cooled and crystallized, and the crystals were filtered, recovered and dried. The product weight was 11.4 g, which was a yield of 57.6%, and the melting point was 63–67° C. The purity of the product was 98% according to liquid chromatography.

EXAMPLE 6

Production of carboxybenzotriazole phenyl ester

In a 300 mL four-necked flask equipped with a thermometer, stirrer and reflux condenser there were charged 18.7 g (0.101 mole) of carboxybenzotriazole sodium salt and 40 g of phenol as a solvent, the internal temperature was raised to 90° C., and 28.0 g (0.12 mole) of diphenyl phosphite was slowly added at a temperature of below 100° C. Heating was initiated while stirring for gradual temperature increase, and carboxybenzotriazole phenyl ester was produced at a temperature of 150–160° C. Upon reaction for 6 hours, the presence of unreacted carboxybenzotriazole sodium salt crystals was no longer apparent, and the reaction was continued for one hour at the same temperature. Analysis of the reaction solution by liquid chromatography showed disappearance of the carboxybenzotriazole sodium salt starting material and an esterification rate of 90%.

After completion of the reaction, the internal temperature was lowered to 120° C., and a distillation condenser was mounted in place of the reflux condenser for distillation removal of the phenol under reduced pressure. The internal temperature was then lowered to 80° C., the reflux condenser was remounted, 50 g of a 50% IPA aqueous solution was added dropwise, and the mixture was allowed to cool. The precipitated crude crystals were filtered off and recovered, and then recrystallized from a 50% IPA aqueous solution. The product weight was 17.8 g, which was a yield of 75%, and the melting point was 172–175° C. The purity of the product was 99% according to liquid chromatography.

EXAMPLE 7

Production of diphenyl sebacate

In a four-necked flask having the same construction as that used in Example 1 there were charged 234 g (1.0 mole) of diphenyl phosphite and 101 g (0.5 mole) of sebacic acid, and reaction was carried out for one hour at 120–130° C. while stirring. Analysis of the reaction solution by liquid chromatography showed an esterification rate of 97%.

The same post-treatment was carried out as in Example 2. The product weight was 134 g, which was a yield of 76%.

As demonstrated above, according to the present invention it is possible to produce carboxylic acid aryl esters easily and inexpensively by a very simple process.

What we claim is:

1. A process for production of carboxylic acid aryl esters which comprises reacting a carboxylic acid having at least one carboxyl group with a di- or tri-aryl phosphite compound represented by the following general formula (1):

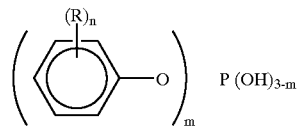 (1)

where each R independently represents a hydrogen atom, halogen or alkyl group, m is 2 or 3 and n is 1, 2, or 3, and when there exist a plurality of halogen and/or alkyl groups as R, they may be the same or different, in the presence of a basic compound and/or water.

2. A process for production of carboxylic acid aryl esters which comprises reacting a basic salt of a carboxylic acid having at least one carboxyl group with a diaryl phosphite compound represented by the following general formula (2):

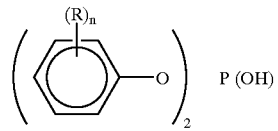 (2)

where each R independently represents a hydrogen atom, halogen or alkyl group, n is 1, 2, or 3, and when there exist a plurality of halogen and/or alkyl groups as R, they may be the same or different.

3. A process for production of carboxylic acid aryl esters which comprises reacting a carboxylic acid having at least one carboxyl group with a diaryl phosphite compound represented by the following general formula (2):

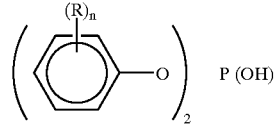 (2)

where each R independently represents a hydrogen atom, halogen or alkyl group, n is 1, 2, or 3, and when there exist a plurality of halogen and/or alkyl groups as R, they may be the same or different.

* * * * *